United States Patent
Bowley

(10) Patent No.: US 9,180,001 B2
(45) Date of Patent: Nov. 10, 2015

(54) METHODS OF BREAST SURGERY

(71) Applicant: C.R. Bard, Inc., Murray Hill, NJ (US)

(72) Inventor: Melissa Bowley, Newport, RI (US)

(73) Assignee: C.R. Bard, Inc., Murray Hill, NJ (US)

(*) Notice: Subject to any disclaimer, the term of this patent is extended or adjusted under 35 U.S.C. 154(b) by 31 days.

(21) Appl. No.: 13/968,832

(22) Filed: Aug. 16, 2013

(65) Prior Publication Data

US 2015/0051623 A1    Feb. 19, 2015

(51) Int. Cl.
*A61F 2/12* (2006.01)
*A61B 17/00* (2006.01)

(52) U.S. Cl.
CPC .............. *A61F 2/12* (2013.01); *A61B 17/00491* (2013.01); *A61F 2220/005* (2013.01); *A61L 2430/04* (2013.01)

(58) Field of Classification Search
CPC ................................. A61F 2/12; A61F 2/0063
USPC .......................................................... 623/7–8
See application file for complete search history.

(56) References Cited

U.S. PATENT DOCUMENTS

| | | |
|---|---|---|
| 5,676,161 A | 10/1997 | Breiner |
| 8,287,566 B2 | 10/2012 | Leopold et al. |
| 2008/0097526 A1 | 4/2008 | Accardo |
| 2010/0305696 A1* | 12/2010 | Mao et al. ................ 623/8 |
| 2012/0177611 A1* | 7/2012 | Blau et al. .................... 424/93.7 |
| 2012/0201890 A1* | 8/2012 | Williams et al. ............. 424/484 |
| 2013/0344500 A1* | 12/2013 | Trautman et al. ............. 435/7.1 |
| 2014/0025104 A1* | 1/2014 | Ishii ............................. 606/213 |
| 2014/0121770 A1* | 5/2014 | Ikeyama et al. ................ 623/8 |
| 2014/0277454 A1* | 9/2014 | Locke et al. ............... 623/15.12 |
| 2014/0288646 A1* | 9/2014 | Khouri et al. .................... 623/8 |

OTHER PUBLICATIONS

Karp, Nolan S., Chapter 58: Mastopexy and Mastopexy Augmentation, Grabb and Smith's Plastic Surgery, 2007, pp. 585-592, Sixth Edition, Lippincott Williams & Wilkins.

* cited by examiner

*Primary Examiner* — Suzette J Gherbi
(74) *Attorney, Agent, or Firm* — Wolf, Greenfield & Sacks, P.C.

(57) ABSTRACT

Surgical procedures of the breast where an adhesive is applied to fixate a reshaped and/or relocated portion of breast tissue.

31 Claims, 14 Drawing Sheets

METHODS OF BREAST SURGERY

FIELD

Aspects relate to methods of breast surgery including, but not limited to, breast lifts, breast reconstructions, breast reductions, and breast augmentations.

DISCUSSION OF RELATED ART

The breasts may begin to sag in response to one or more of various factors. During aging, the skin around the breast loses elasticity due to a gradual breakdown of the skin's support network. The suspensory ligaments that attach the breast to the chest wall may weaken and stretch in response to gravity. During pregnancy and/or breast feeding, the breasts may enlarge, which may cause the skin to stretch. As the breasts reduce in size following pregnancy, the skin that was once stretched may become loose. Also, fluctuations in weight and hormonal changes may cause breasts to change in appearance.

A breast lift, or mastopexy, can help restore the size, contour and/or elevation of sagging breasts. In conventional mastopexy, internal sutures are used to fixate breast tissue that has been reshaped and/or elevated. Conventional mastopexy techniques may rely upon the skin at the lower pole of the breast to support the lifted breast tissue. As used herein, the lower pole of the breast is the portion of the breast that lies inferior to the center of the areola, while the upper pole of the breast is the portion of the breast that lies superior to the center of the areola.

SUMMARY

According to one embodiment, a method of treating breast tissue involves moving a portion of breast tissue from a first location to a second location. An adhesive is applied to retain the first portion of breast tissue at the second location.

According to another embodiment, a method of treating breast tissue involves shaping a first portion of breast tissue from a first form into a second form. An adhesive is applied to retain the first portion of breast tissue in the second form.

According to another embodiment, a method of treating breast tissue involves applying an adhesive to either a prosthetic for a breast, such as a surgical fabric or a breast implant, or to a portion of breast tissue.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. Various embodiments of the invention will now be described, by way of example, with reference to the accompanying drawings, in which.

DETAILED DESCRIPTION

Applicant has appreciated that internal sutures used during conventional mastopexy, and other surgical procedures involving the breast, may lead to complications such as pain and infection. In addition, internal sutures may be palpable through the skin and be mistaken for cancerous breast lumps. Furthermore, conventional breast lift or breast reduction repair procedures have recurrent ptosis rates as high as 27%. Applicant has recognized that a possible reason for such a high recurrence rate is that conventional procedures rely on the weak skin at the lower pole of the breast to support the lifted and/or reshaped breast.

Provided herein are embodiments where a method of performing a breast lift, breast reduction, breast augmentation, or other breast procedure uses an adhesive to fixate breast tissue that has been reshaped and/or relocated. The skin and breast tissue at the upper pole may be adhered by adhesive, reducing the tension on the skin at the lower pole and, consequently, enhancing healing and delaying or reducing recurrence of ptosis. The following description details the use of an adhesive during a mastopexy procedure, but it should be appreciated that an adhesive may be used during any suitable breast procedure, such as, but not limited to, mammoplasty, breast augmentation, and breast reconstruction.

During mastopexy, loose, excess skin is removed, and the remaining skin is tightened. Generally, the amount of skin removed is based upon the degree of ptosis of the breasts. Four common breast lift techniques include the periareolar, circumareolar, vertical, and anchor procedures. In each such procedure, it is customary to employ internal sutures to fixate reshaped and/or repositioned breast tissue. Additionally, or alternatively, it is conventional to suture together skin and breast tissue.

Figure 1A:
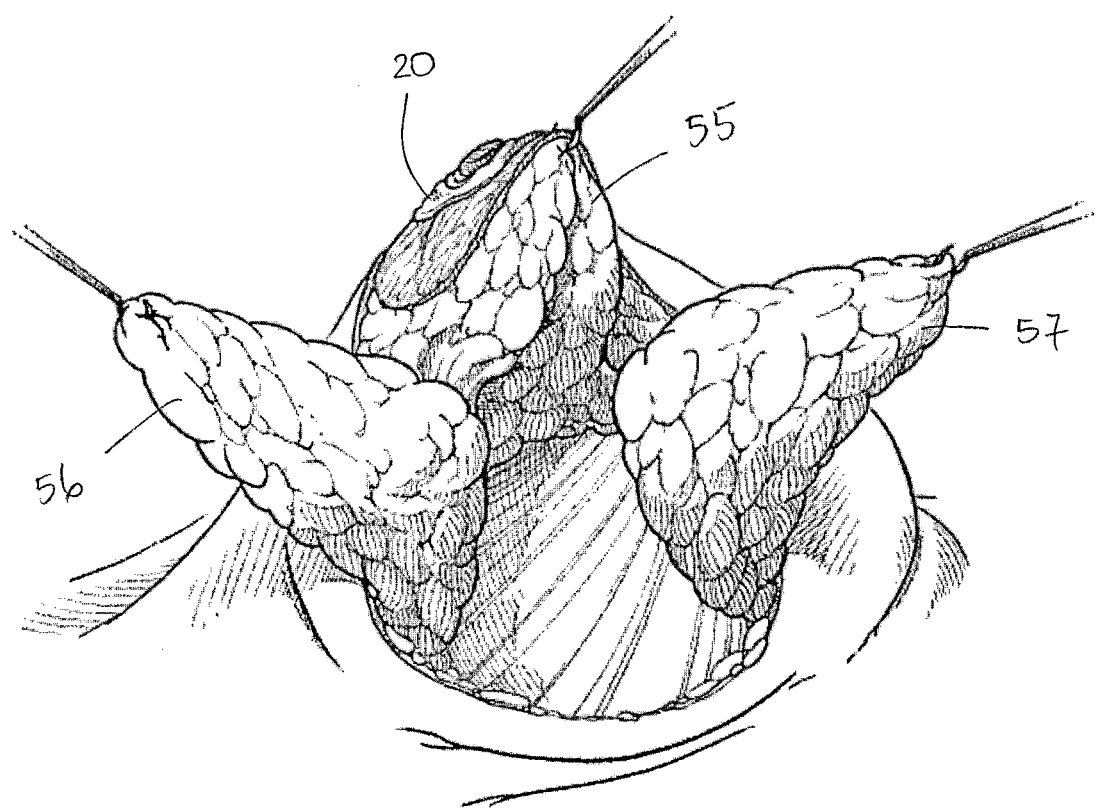
FIGS. 1A-1E depict a conventional mastopexy technique.
Figure 1B:
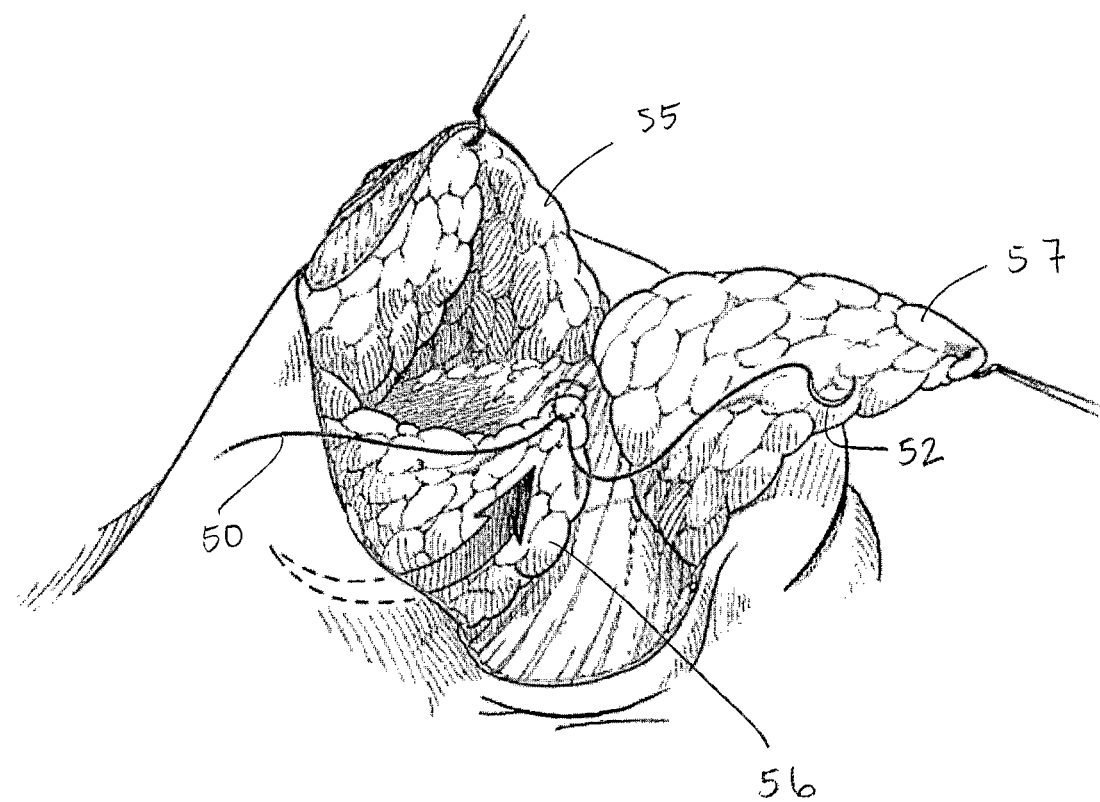
Figure 1C:
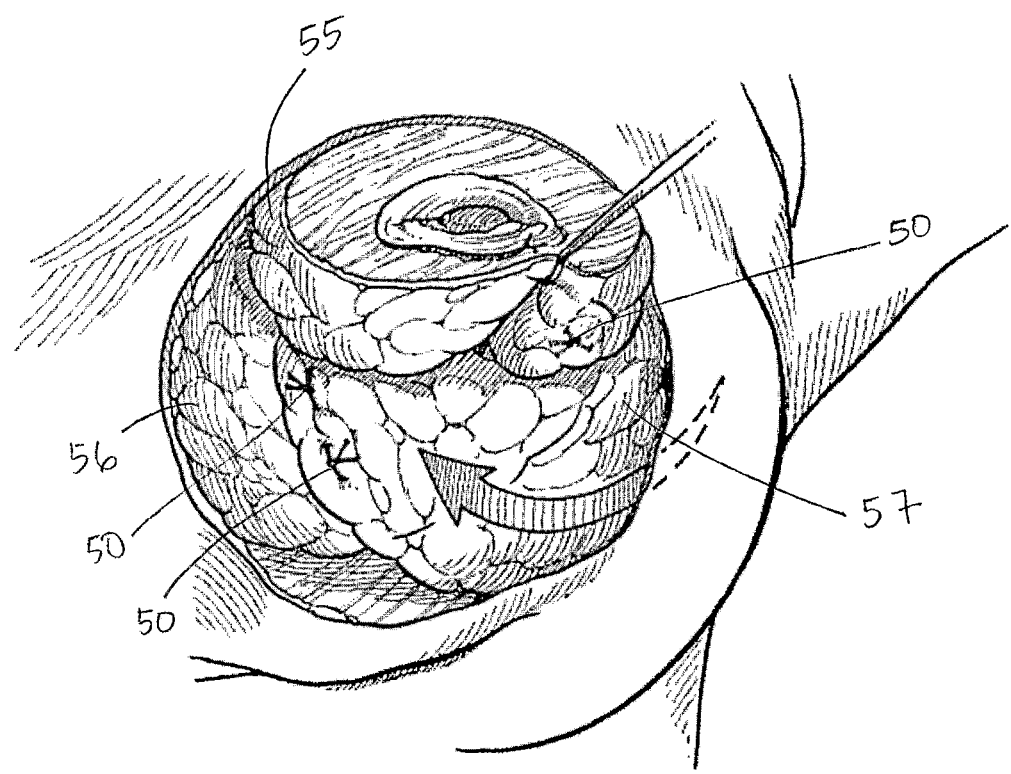
Figure 1D:
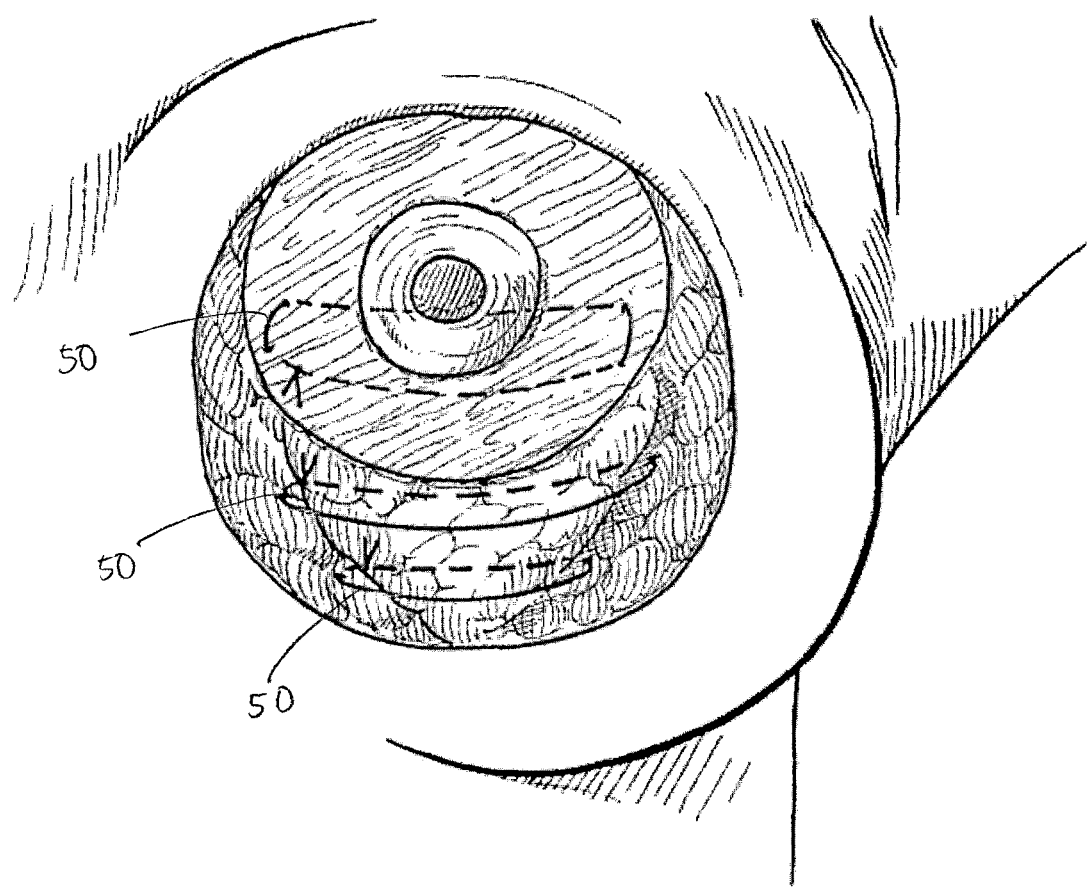
Figure 1E:
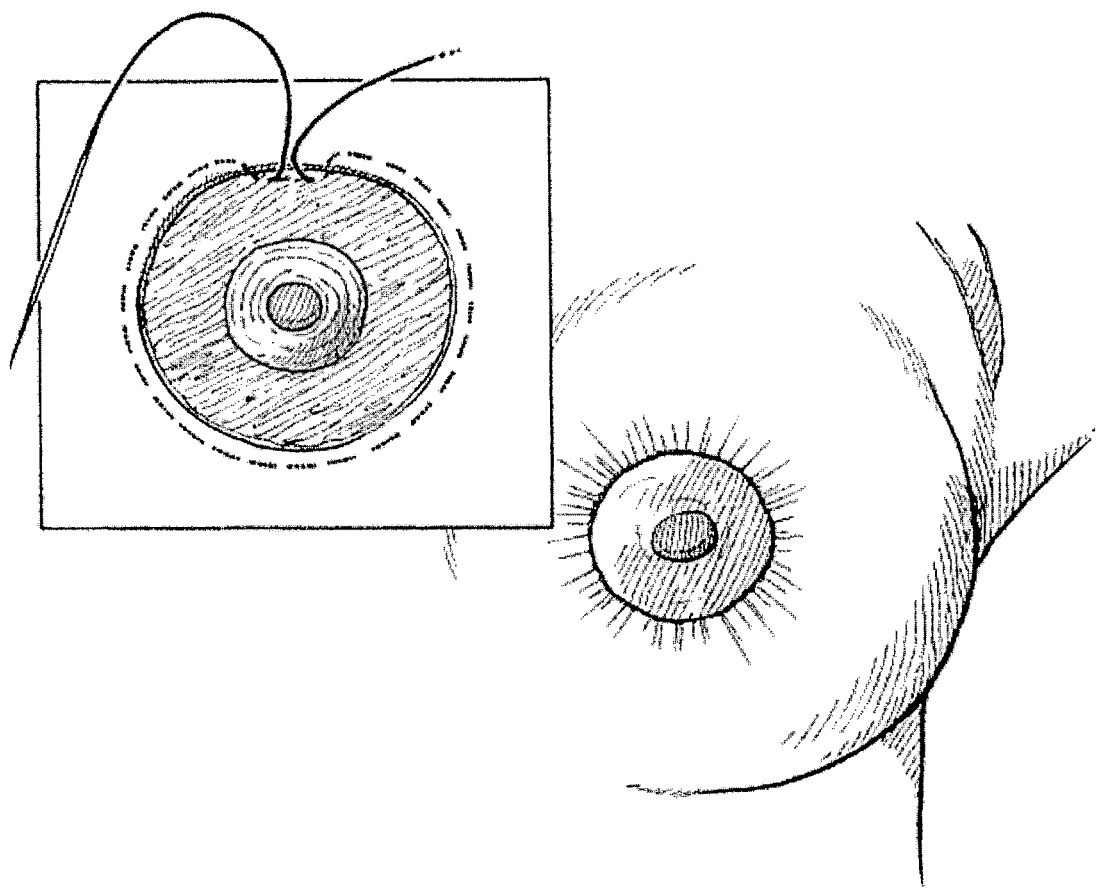

FIGS. 1A-1E depict a conventional Benelli mastopexy procedure (circumareolar), which uses internal sutures. Generally, during the Benelli mastopexy procedure, the surgeon cuts the breast gland to form multiple flaps, then criss-crosses the flaps and sutures the flaps together to create a conical breast shape. As seen in FIG. 1A, the breast gland has been cut into glandular flaps 55, 56, 57, where the areola 20 is based on the superior flap 55. As seen in FIG. 1B, the medial flap 56 is rotated and sutured into its desired location using a suture needle 52 and suture 50. As seen in FIG. 1C, the lateral flap 57 is rotated and sutured over the medial flap 56 using suture 50. Suture 50 on the superior flap 55 may also be used to shape the superior flap 55 and/or suture the superior flap 55 to the lateral flap 57. As seen in FIG. 1D, the conical shape of the breast is supported by full-breast lacing using sutures 50. Finally, as seen in FIG. 1E, the incision is closed by using a round-block purse-string suture.

According to one aspect of the invention, an adhesive is used to retain the shape and/or position of moved breast tissue rather than internal sutures. A conventional skin incision may be used to access the breast tissue. Adhesive may be applied in various locations, as well as at various points in time during the procedure. In addition to the act of applying an adhesive, the procedure may include one or a combination of the following acts in any suitable order: moving a portion of breast tissue from a first location to a second location, and shaping the breast tissue into a desired form. The act of applying an adhesive involves applying an adhesive directly, indirectly, or may be applied both directly and indirectly. For example, applying an adhesive indirectly to breast tissue includes applying adhesive to an area that is not on the breast tissue, and then contacting the breast tissue with the area in which adhesive was applied before the adhesive has completely cured. Such an area may be part of an anatomical structure or a prosthetic device, such as a surgical repair fabric or a breast implant. Where adhesive is applied both directly and indirectly, the adhesive may be applied simultaneously both directly and indirectly, or at separate intervals. Adhesive may be applied intermittently whether directly, indirectly, or both directly and indirectly.

Figure 2:
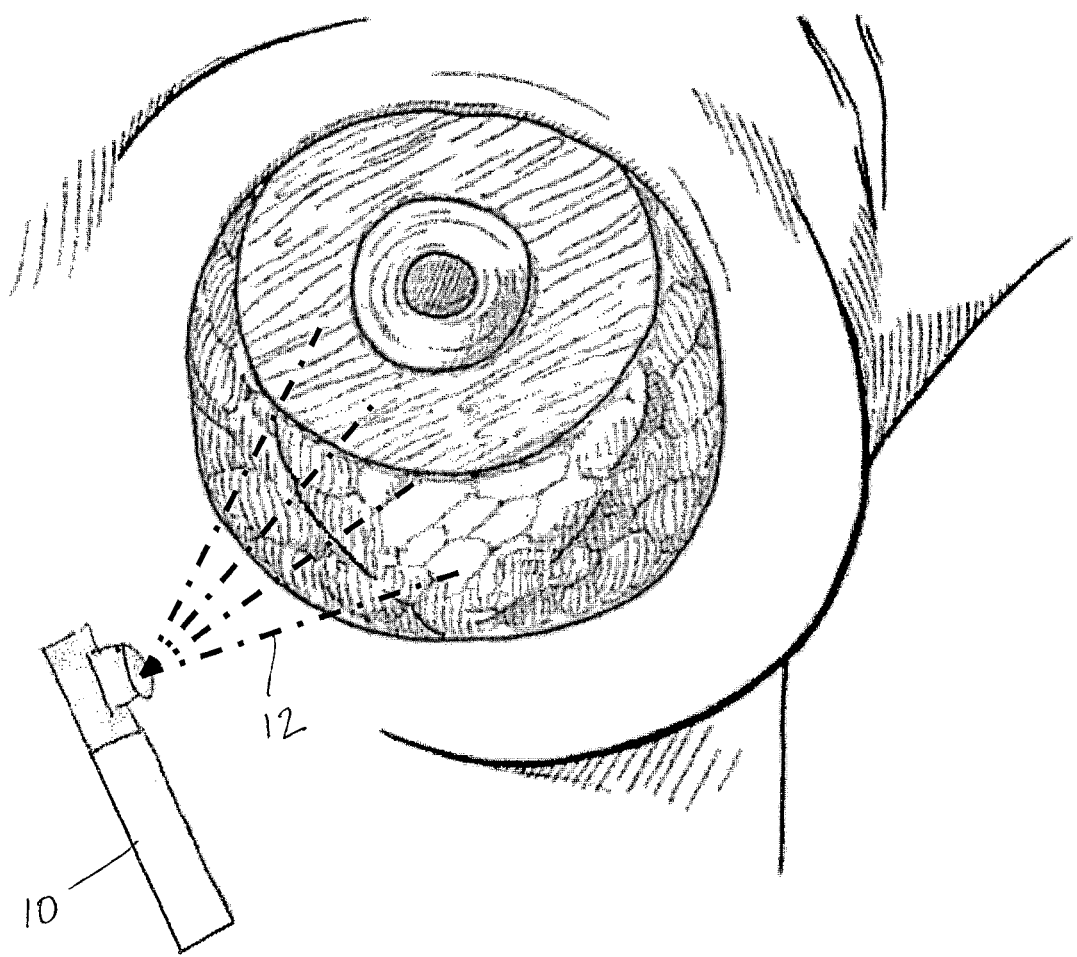
FIG. 2 depicts a surgical procedure using an adhesive in accordance with an aspect of the invention.

In one embodiment, a portion of breast tissue is moved from a first location to a second location, the breast tissue is shaped into a desired form at the second location, and an adhesive is applied. In one illustrative embodiment shown in FIG. 2, the glandular flaps have already been moved to a new location and shaped into a desired form. With the reshaped breast tissue held at the new location, an adhesive 12 is applied to fixate the entire mass. An application 10 may be used to apply the adhesive. The adhesive may serve as a supportive, bra-like structure, that retains the lifted breast tissue in a particular shape at a desired location, thereby eliminating the need for internal sutures.

In another embodiment, a portion of breast tissue is moved from a first location to a second location, adhesive is applied, and then the portion of breast tissue is shaped. The adhesive may be applied directly to the portion of breast tissue itself. Alternatively or in addition, the adhesive may be applied indirectly to the portion of breast tissue by applying the adhesive to an anatomical structure, and then contacting the portion of breast tissue and the area of the anatomical structure where adhesive was applied. As used herein, anatomical structure includes, but is not limited to, other breast tissue, the internally facing side of skin overlying the portion of breast tissue, the chest wall and the periosteum of the ribs. A portion of breast tissue may be shaped into any suitable form in any suitable way, as this aspect is not so limited. As illustrative, non-limiting examples, the portion of breast tissue may be shaped by folding the breast tissue onto itself, curling it into a roll, bending the breast tissue to form a curve, or flattening the breast tissue.

Figure 3:
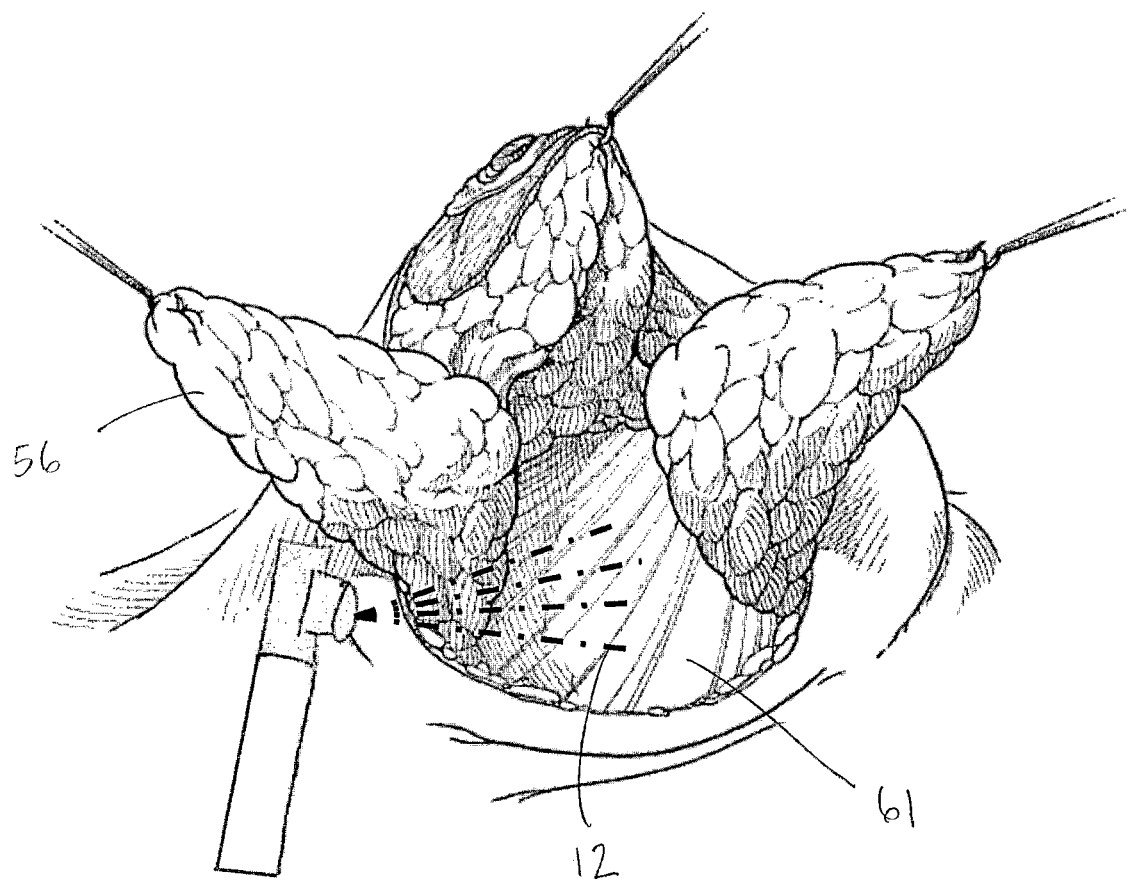
FIG. 3 depicts the application of an adhesive to a chest wall.

In yet another embodiment, an adhesive is applied, a portion of breast tissue is moved from a first location to a second location, and then the portion of breast tissue is shaped. The adhesive may be applied directly or indirectly to the portion of breast tissue, or may be applied both directly and indirectly. To apply the adhesive indirectly to the portion of breast tissue, the surgeon applies adhesive to anatomical structures that will surround the portion of breast tissue once the portion of breast tissue is moved to its desired location. When the portion of breast tissue is moved to the desired location, the surgeon may contact the portion of breast tissue to the areas where adhesive was applied. In one illustrative example shown in FIG. 3, adhesive is applied indirectly to a portion of breast tissue. Adhesive 12 is applied to the chest wall 61. The surgeon moves medial flap 56 in contact with the area of the chest wall 61 where adhesive was applied. Once the medial flap 56 has been moved to its new location, the surgeon may optionally shape the flap into a desired form.

Figure 4:
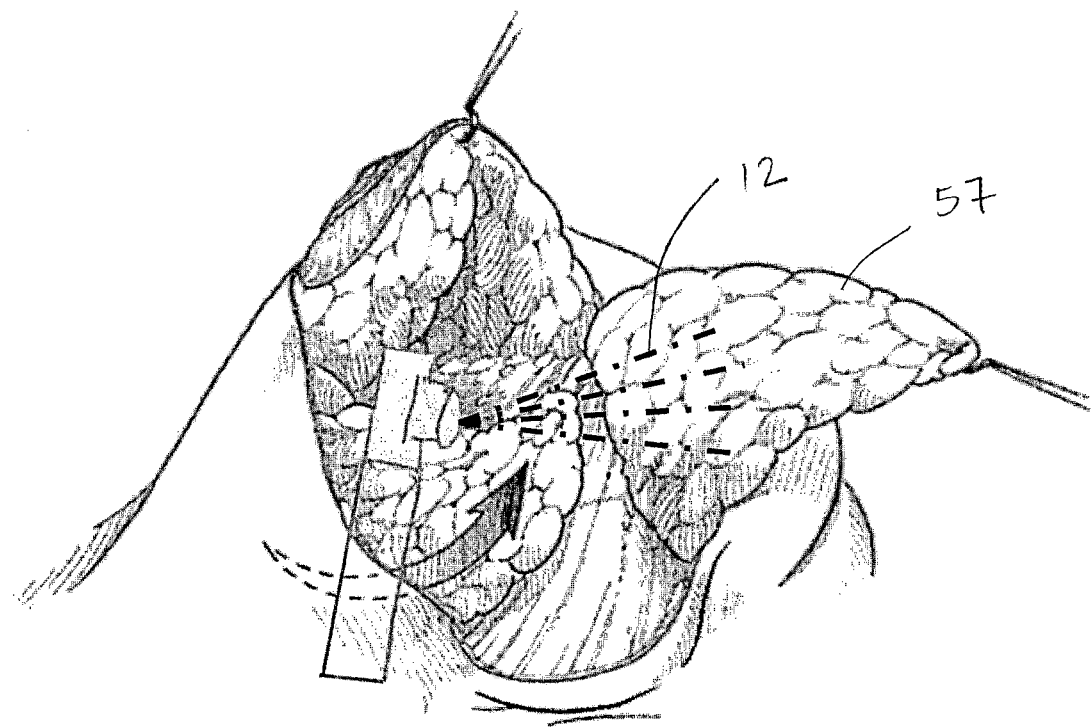
FIG. 4 depicts the application of an adhesive to a lateral flap of breast tissue.

In yet another embodiment, an adhesive is applied, a portion of breast tissue is shaped, and then the shaped portion of breast tissue is moved from a first location to a second location. The adhesive may be applied directly or indirectly to the portion of breast tissue, or may be applied both directly and indirectly. In one illustrative example shown in FIG. 4, adhesive is applied directly to a portion of breast tissue. Adhesive 12 is applied to the lateral flap 57. The surgeon shapes the lateral flap 57 into a desired form. The adhesive that was applied to the lateral flap 57 may help the lateral flap 57 retain its shape. The surgeon may move the shaped lateral flap 57 to a desired location. Additional adhesive may be used to retain the shaped lateral flap at a desired location.

Figure 5:
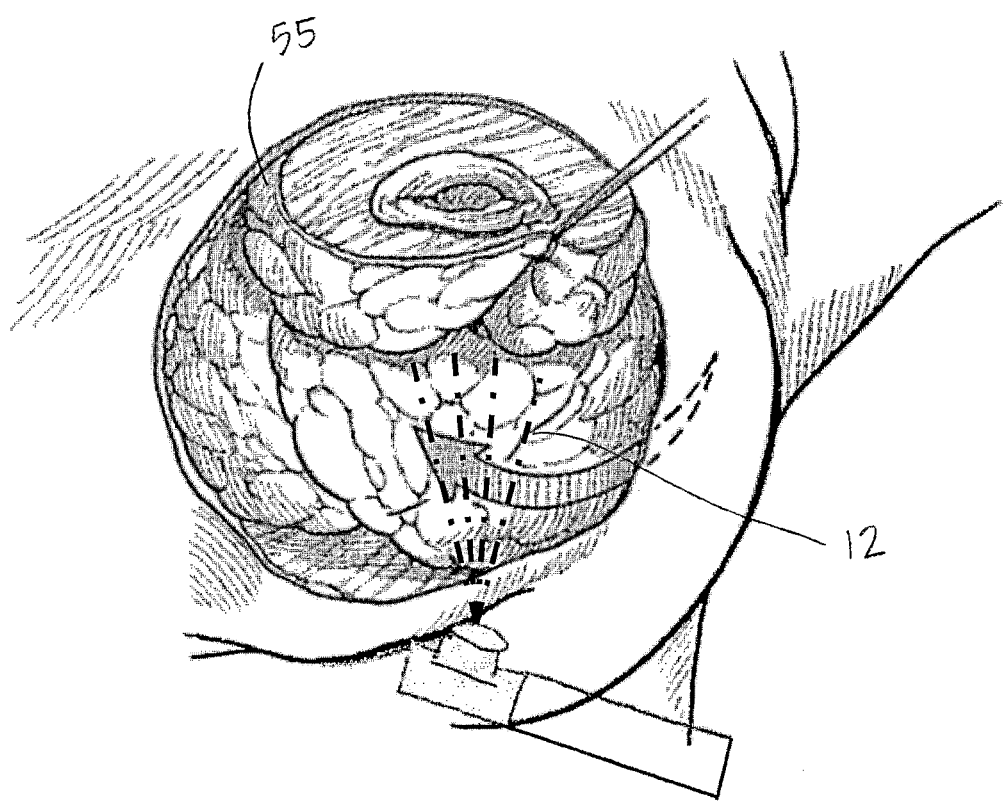
FIG. 5 depicts the application of an adhesive to breast tissue.

In yet another embodiment, a portion of breast tissue is shaped, the shaped portion of breast tissue is moved to a desired location, and then an adhesive is applied. The adhesive may be applied directly or indirectly to the portion of breast tissue, or may be applied both directly and indirectly. In one illustrative example shown in FIG. 5, the superior flap 55 has already been moved to a desired location and shaped into the desired form. Adhesive 12 is then applied to retain the shape and location of the superior flap 55.

In yet another embodiment, a portion of breast tissue is shaped, an adhesive is applied, and then the shaped portion of breast tissue is moved to a desired location. The adhesive may be applied directly or indirectly to the portion of breast tissue, or may be applied both directly and indirectly.

In yet another embodiment, a portion of breast tissue may be shaped without necessarily moving the breast tissue from a first location to a second location. For example, a glandular flap may be rolled or otherwise formed into a particular shape, but may remain in the same location after the shape transformation. Adhesive may be applied directly, indirectly, or both directly and indirectly, whether before, after, or during the shaping of the portion of breast tissue, or any combination thereof.

In yet another embodiment, a portion of breast tissue is moved from a first location to a second location. An adhesive may be applied directly, indirectly, or both directly and indirectly, to the portion of breast tissue or to an anatomical structure or a prosthetic device (such as a surgical fabric or a breast implant) at the second location, to fixate the breast tissue at the second location.

In some embodiments, two or more portions of breast tissue may be repositioned and/or reshaped. In one embodiment, a first portion of breast tissue is adhered to a second portion of breast tissue. The first and second portions of breast tissue may each be manipulated as in any of the embodiments described above. In addition, adhesive may be applied to retain the first and second portions of breast tissue together. In some embodiments, adhesive is applied directly to one or both of the portions of breast tissue, and then the two portions are pressed in contact with one another. In one illustrative example shown in FIG. 6, adhesive 12 is applied to the anterior aspect of the medial flap 56. The medial flap 56 may then be pressed in contact with the lateral flap 57 to retain the two flaps together. Alternatively or in addition, the two portions of breast tissue may be placed in contact with one another, and then adhesive may be applied to both portions of breast tissue while the two portions are held in contact with one another.

In some embodiments, adhesive may be applied during the acts of moving and/or shaping the portion of breast tissue. For example, while shaping the portion of breast tissue, the surgeon may intermittently or continuously apply adhesive to the portion of breast tissue. While moving the breast tissue from a first location to a second location, adhesive may be applied to an anatomical structure and/or to the portion of breast tissue itself, and once the portion of breast tissue is placed in the second location, additional adhesive may be applied to retain the portion of breast tissue to the second location. Alternatively, or in addition, adhesive may be applied to a prosthetic, such as a surgical fabric or a breast implant, that is locatable relative to the second location.

Figure 6:
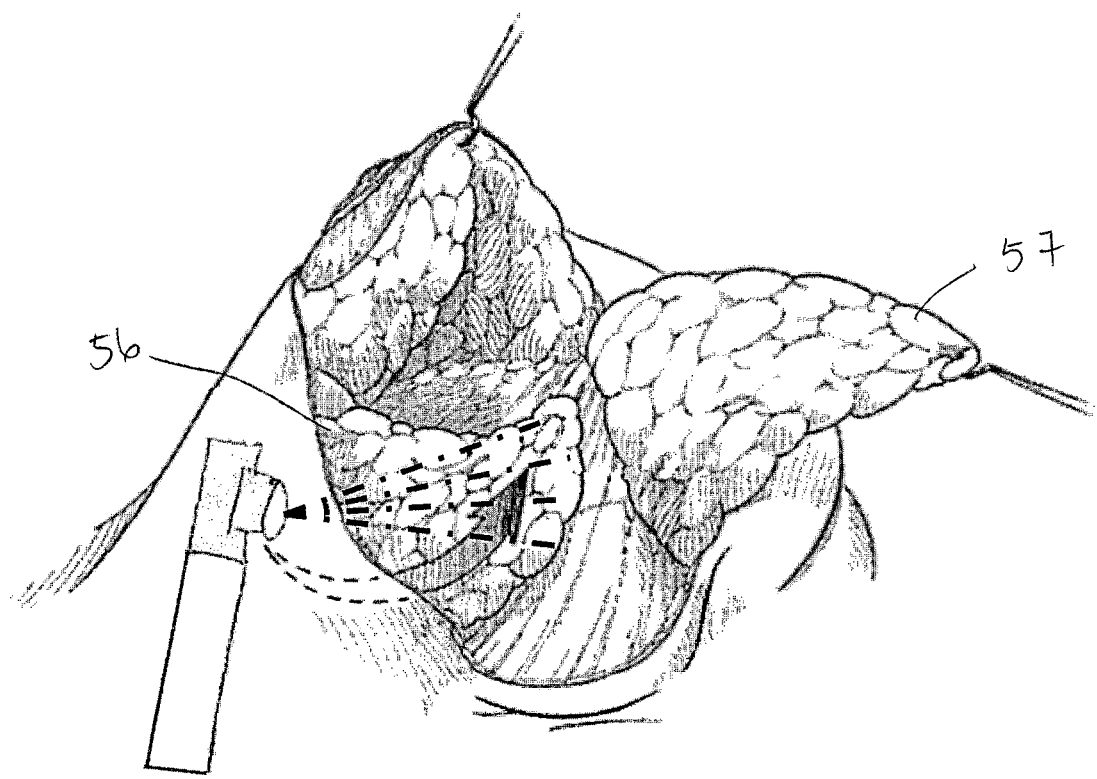
FIG. 6 depicts the application of an adhesive to a medial flap of breast tissue.
Figure 7:
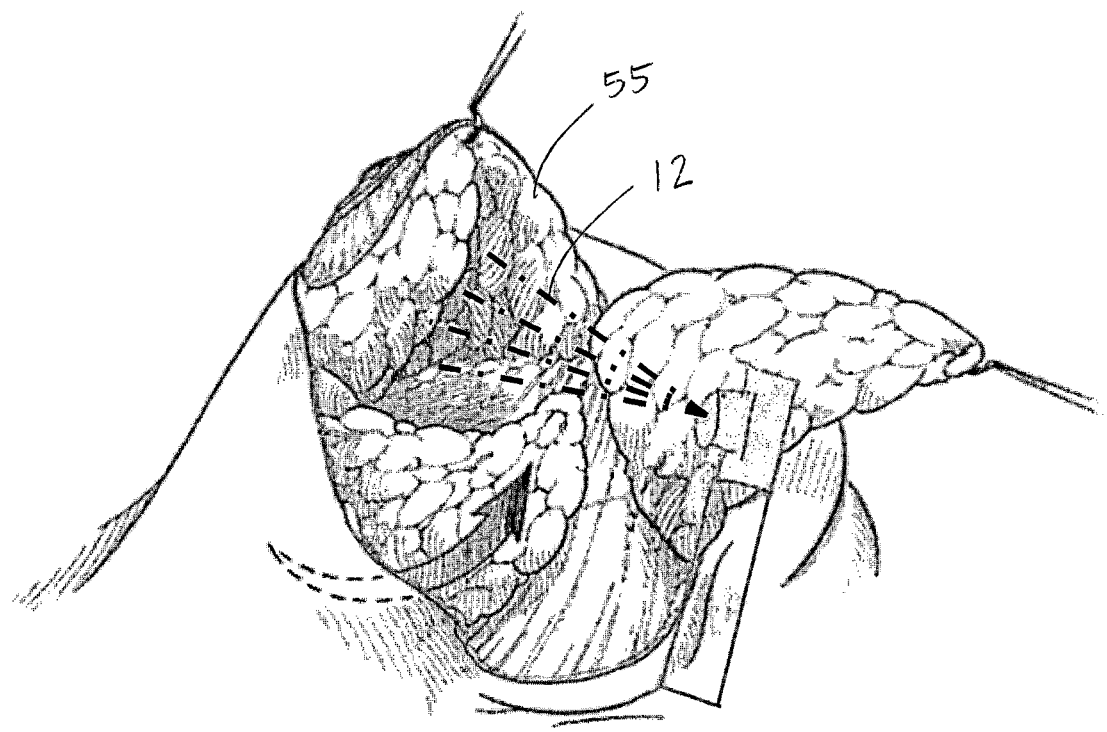
FIG. 7 depicts the application of an adhesive to a superior flap of breast tissue.

It should be appreciated that adhesive can be applied on any suitable portion of an anatomical structure, prosthetic, and/or the portion of breast tissue that is being manipulated. For example, as shown in FIG. 6, adhesive 12 is applied to the anterior aspect of the medial flap 56. In another illustrative example shown in FIG. 7, adhesive 12 is applied to the posterior aspect of the superior flap 55.

Figure 8:
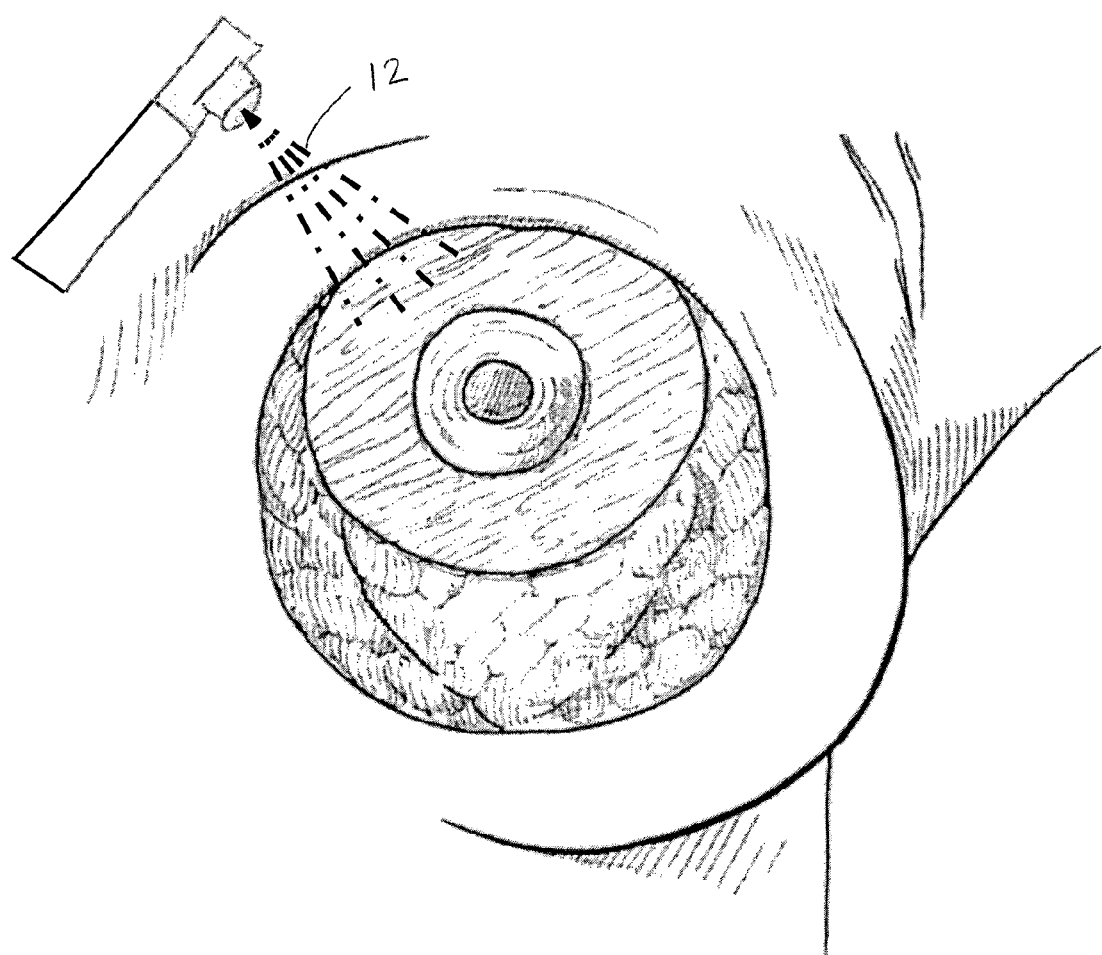
FIG. 8 depicts the application of an adhesive to breast tissue.

In some embodiments, adhesive is used to adhere the breast tissue to the skin overlying the breast tissue. In one illustrative example, as shown in FIG. 8, adhesive 12 is applied to the breast tissue prior to closure of the incision. The internally facing side of the skin overlying the breast tissue is then pressed in contact with the area where adhesive was applied. Alternatively or in addition, adhesive may be applied directly to the internally facing side of the skin overlying the breast tissue. Adhesive may be used anywhere on the breast, including the lower pole region and/or the upper pole region. Adhering the lifted breast tissue to the skin at the upper and/or lower pole regions of the breast may help to support the repositioned and/or reshaped breast tissue. In some cases, adhering the breast tissue to the skin of the upper pole of the breast may help to reduce the amount of tension on the skin of the lower pole of the breast. A prosthetic, such as a surgical repair fabric, may be located between the skin and the breast tissue. Adhesive may be applied between one or both of the skin and prosthetic and breast tissue and the prosthetic.

Figure 9:
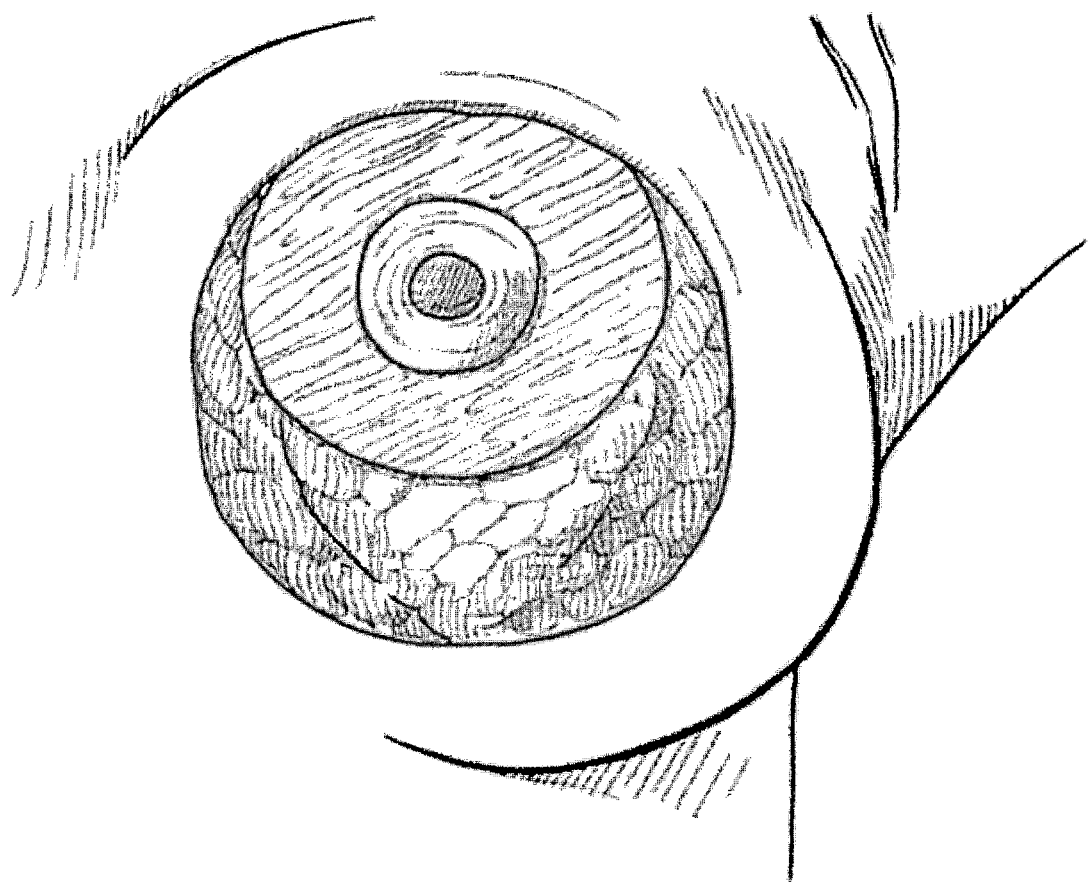
FIG. 9 depicts shaped and repositioned breast tissue prior to closure of the skin incision.

As seen in FIG. 9, by using an adhesive, the breast tissue is retained in a repositioned and reshaped form without the use of internal sutures. The incision may then be closed.

Figure 10:
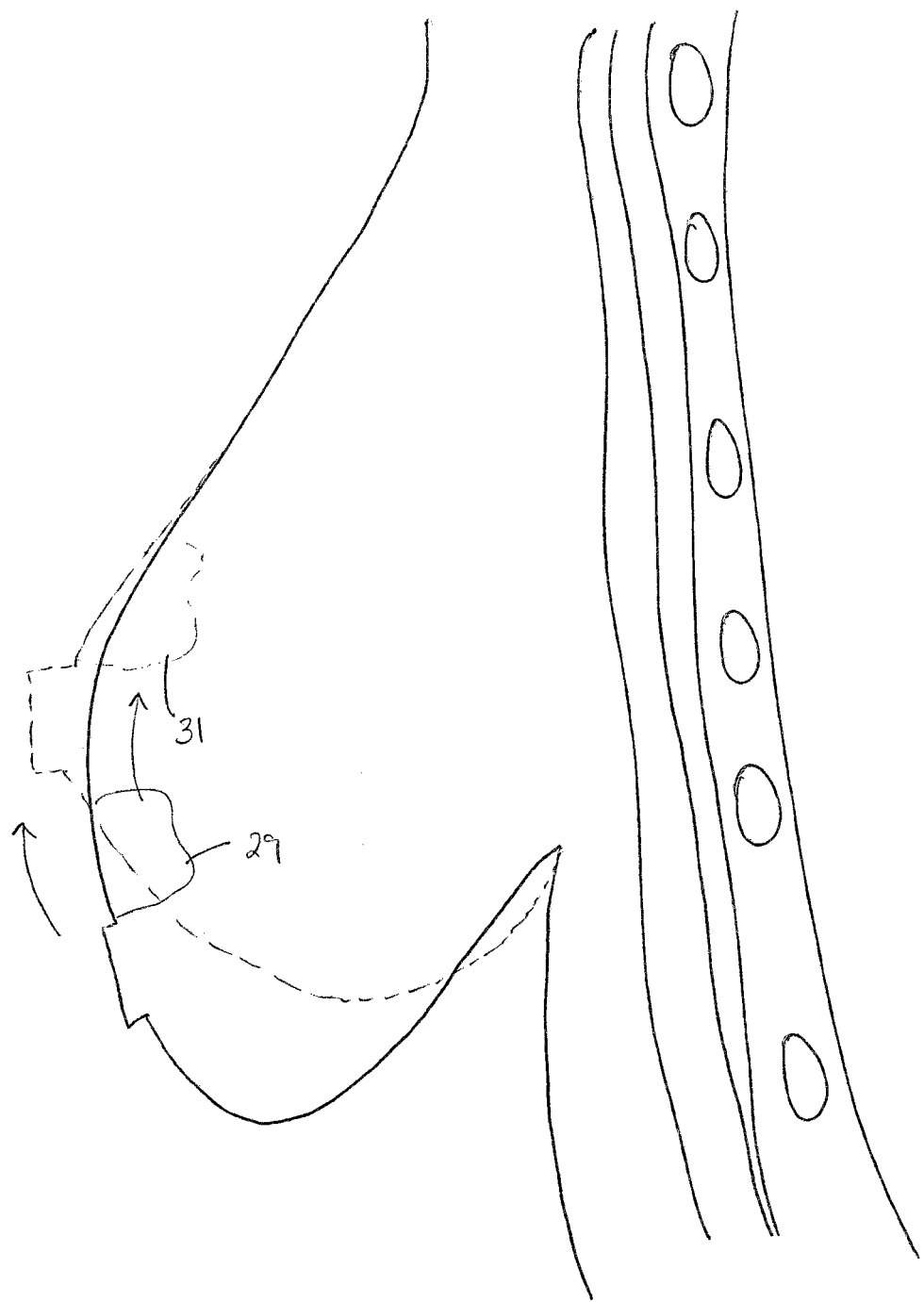
FIG. 10 is a side view of a breast that depicts a portion of breast tissue being lifted from a first location to a second location.

As shown in FIG. 10, as a result of one of more of the embodiments described above, a portion of breast tissue may move from a first location 29 to a second, more upright target location 31. In FIG. 10, solid lines show the breast in the first position, and dashed lines show the breast in the more upright position. In some embodiments, the second location 31 may be anatomically superior to the first original location 29—that is, the second location 31 is closer to the head of the patient than is the first location 29.

In some embodiments, allogenic, xenogenic, or other replacement breast tissue, rather than autologous breast tissue, may be moved from a first position to a second position, shaped from a first form to a second form, and/or otherwise manipulated, and then retained or secured in such new position, and/or form, via an adhesive. In yet other embodiments, adhesive may be used to fixate a prosthetic, whether a surgical repair fabric, a breast implant, or otherwise. In some embodiments, the prosthetic is at least partially surrounded and/or supported by a tissue pocket or a tissue-simulative pocket, where such pocket may be adhered to an anatomical structure using an adhesive or may be at least partially constructed using an adhesive. Alternatively or in addition, the prosthetic may be adhered to such a pocket with an adhesive.

According to another aspect, the adhesive may be any suitable adhesive that is biocompatible and capable of supporting a tissue load. The adhesive may be permanent or it may be resorbable. The adhesive may be sprayable, may be a film, a paste, a dry form, or any suitable form, as this aspect is not limited in this regard. Examples of sprayable adhesive include, but are not limited to: PROGEL or other hydrogel adhesive, fibrin glue, and cyanoacrylate based adhesives. Examples of film adhesive include, but are not limited to: hydrogel based adhesives in film form. Examples of paste adhesives include, but are not limited to: fibrin based adhesives and hydrogel based adhesives. A dry form adhesive may be hydrated upon contact with biologic tissue or by a separate act of hydration. Examples of dry form adhesives include, but are not limited to: fibrin based adhesives and hydrogel based adhesives. Film and/or paste adhesives may be activated by water, temperature and/or cross-linking agents.

In some embodiments, the adhesive may have a cure time that allows a surgeon to adjust the location and/or shape of a portion of breast tissue after the adhesive has been applied. In such embodiments, the adhesive may have a cure time of about 1 to 5 minutes. In other embodiments, the adhesive may have a very short cure time such that the portion of breast tissue cannot easily be moved after the adhesive has been applied.

The above aspects and embodiments may be employed in any suitable combination, as the present invention is not limited in this respect.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method of performing a surgical procedure involving the breast, comprising:
    moving a first flap of tissue from a first location to an anatomical structure at a second location; the anatomical structure comprising at least one of skin overlying breast tissue, breast tissue, chest wall, rib periosteum, and skin at an upper pole portion of a breast; and
    applying an adhesive to retain the first flap of tissue at the second location.

2. The method of claim 1, wherein the adhesive is applied to the first flap of tissue.

3. The method of claim 1, wherein the adhesive is applied to the anatomical structure.

4. The method of claim 3, wherein the adhesive is applied to the anatomical structure before the first flap of tissue is moved to the second location.

5. The method of claim 4, further comprising contacting the first flap of tissue with the anatomical structure.

6. The method of claim 2, wherein the adhesive is applied to the first flap of tissue after the first flap of tissue is moved to the second location.

7. The method of claim 1, wherein the adhesive is applied to a prosthetic.

8. The method of claim 7, wherein the prosthetic is selected from the group consisting of a surgical repair fabric and a breast implant.

9. The method of claim 1, wherein the second location is anatomically superior to the first location.

10. The method of claim 1, further comprising moving a second flap of tissue from a third location to a fourth location; and
    applying an adhesive to retain the second flap of tissue at the fourth location.

11. The method of claim 10, wherein the second flap of tissue is placed adjacent to the first flap of tissue after the first flap of tissue is moved to the second location.

12. The method of claim 11, further comprising applying an adhesive to retain the second flap of tissue to the first flap of tissue.

13. The method of claim 12, wherein the act of applying an adhesive to retain the second flap of tissue to the first flap of tissue comprises applying adhesive to one of the first or second flaps of tissue, then contacting the second flap of tissue with the first flap of tissue.

14. The method of claim 12, wherein the act of applying an adhesive to retain the second flap of tissue to the first flap of tissue comprises placing the second flap of tissue in contact with the first flap of tissue, then applying adhesive to both the first and second flaps of tissue.

15. A method of performing a surgical procedure involving the breast, comprising:
    shaping a first flap of breast tissue from a first form into a second form; and
    applying an adhesive to retain the first flap of breast tissue in the second form.

16. The method of claim 15, wherein the adhesive is applied to the first flap of breast tissue.

17. The method of claim 15, wherein the adhesive is applied to the first flap of breast tissue in the second form.

18. The method of claim 15, wherein the adhesive is applied to an anatomical structure.

19. The method of claim 18, wherein the adhesive is applied to the anatomical structure before the first flap of breast tissue is shaped into the second form.

20. The method of claim 18, further comprising contacting the first flap of breast tissue with the anatomical structure.

21. The method of claim 18, wherein the anatomical structure comprises at least one of skin overlying breast tissue, breast tissue, chest wall, rib periosteum, and skin at an upper pole portion of a breast.

22. The method of claim 15, wherein the adhesive is applied to a prosthetic.

23. A method of performing a surgical procedure involving the breast, comprising:
    applying an adhesive to at least one of a prosthetic and a first flap of tissue; and
    attaching the at least one of a prosthetic and a first flap of tissue to an anatomical structure via the applied adhesive, the anatomical structure comprising at least one of skin overlying breast tissue, breast tissue, chest wall, rib periosteum and skin at an upper pole portion of a breast.

24. The method of claim 23, wherein the act of applying an adhesive includes applying an adhesive to an area and then contacting the at least one of a prosthetic and a first flap of tissue with the area including the applied adhesive.

25. The method of claim 23, wherein the act of applying an adhesive includes applying an adhesive to the prosthetic and to the first flap of tissue.

26. A method of treating breast tissue, comprising:
    moving a first portion of breast tissue from a first location to a second location; and
    applying an adhesive to retain the first portion of breast tissue at the second location,
    wherein the second location is anatomically superior to the first location.

27. The method of claim 26, wherein moving the first portion of breast tissue from the first location to the second location comprises moving the first portion of breast tissue from the first location to an anatomical structure at a second location, the anatomical structure comprising at least one of skin overlying breast tissue, breast tissue, chest wall, rib periosteum, and skin at an upper pole portion of a breast.

28. The method of claim 26, wherein the first portion of breast tissue comprises a first flap of breast tissue.

29. The method of claim 26, wherein the adhesive is applied to the first portion of breast tissue.

30. The method of claim 26, wherein the adhesive is applied to the second location.

31. The method of claim 27, wherein the adhesive is applied to the anatomical structure.

* * * * *